United States Patent [19]

Kemp

[11] Patent Number: 4,942,966

[45] Date of Patent: Jul. 24, 1990

[54] CONTAINMENT DEVICE FOR A TEST TUBE

[76] Inventor: David R. Kemp, 2213 Richmond Rd., Paradise, Calif. 95969

[21] Appl. No.: 361,635

[22] Filed: Jun. 5, 1989

[51] Int. Cl.⁵ .............................................. B65D 85/42
[52] U.S. Cl. .................................... 206/521; 206/446; 215/306; 220/375
[58] Field of Search ............... 206/443, 446, 521, 523, 206/583, 586, 591, 592, 594, 588; 220/375; 215/306; 435/294, 296, 810; 422/102, 104

[56] References Cited

U.S. PATENT DOCUMENTS

| | | | |
|---|---|---|---|
| 1,977,580 | 10/1934 | Grier | 206/63.5 |
| 2,812,231 | 11/1957 | Zar | 422/102 X |
| 2,958,439 | 11/1960 | Yochem | 220/375 X |
| 3,001,639 | 9/1961 | Addis | 206/588 |
| 3,275,180 | 9/1966 | Optner et al. | 206/459 X |
| 3,346,135 | 10/1967 | Haitsch . | |
| 3,419,179 | 12/1968 | Deuschle et al. | 220/375 X |
| 3,593,909 | 7/1971 | Bergmann | 220/352 X |
| 3,621,994 | 11/1971 | Brown | 206/446 |
| 3,819,081 | 6/1974 | Runte | 229/93 X |
| 3,826,358 | 7/1974 | Butler et al. | 206/523 X |
| 4,015,941 | 4/1977 | Kurata | 422/102 |
| 4,061,226 | 12/1977 | Essen | 220/339 X |
| 4,132,225 | 1/1979 | Whattan | 220/375 X |
| 4,220,249 | 9/1980 | Nilsson | 220/375 X |
| 4,304,869 | 12/1981 | Dyke | 206/219 X |
| 4,390,111 | 6/1983 | Robbins et al. | 220/375 X |
| 4,501,360 | 2/1985 | Levy et al. . | |
| 4,842,153 | 6/1989 | Hulon | 206/523 X |

FOREIGN PATENT DOCUMENTS

| | | | |
|---|---|---|---|
| 100252 | 2/1965 | Denmark | 206/521 |
| 2749701 | 5/1979 | Fed. Rep. of Germany | 206/523 |
| 3296999 | 5/1984 | Fed. Rep. of Germany | 206/521 |
| 563634 | 7/1957 | Italy | 206/523 |
| 320419 | 1/1972 | U.S.S.R. | 206/521 |
| 557129 | 11/1943 | United Kingdom | 206/523 |

Primary Examiner—Bryon P. Gehman

[57] ABSTRACT

A containment device for protecting an encased test tube holding a biological sample such as a blood or a urine specimen. The device is in the form of a cap-sealed tubular housing which maintains the test tube securely in a reduced bore section towards a structurally closed end. A wide section from the cap sealed end of the container to the reduced bore section permits free access to the upper section of the test tube. This allows the test tube to be predictively retrieved without the rubbery test tube cap restrictively skidding along the wall of the container. Clear plastic having shatter resistant qualities is the preferred material for structuring the container tube. The device provides containment for a specimen filled test tube so the specimen can be safely transported or stored for future analysis or for evidence in a court of law.

3 Claims, 2 Drawing Sheets

CONTAINMENT DEVICE FOR A TEST TUBE

BACKGROUND OF THE INVENTION

1. Field of the Invention

This invention relates to containers for the safe storage and transportation of test tubes. More particularly, the invention is an elongated plastic cylinder with a hinged lid designed for safe retention of a single test tube and to allow easy retrieval of the test tube.

2. Description of the Prior Art

Test tubes containing biological samples such as blood and urine specimens often have to be transported significant distances from a collection site to where the sample is analyzed. Many of these test tubes are depositories for samples requiring storing for future use as evidence in criminal court cases. At the present time, single test tubes containing samples are vulnerable to breakage as very little in the way of protective containment devices for single test tubes is available. Although multiple test tube holders and containers are provided for lab work and shipping, these multiple containers are not adequately configured for protecting the base of a test tube and preventing the rubbery cap from in-container contact during removal. Multiple test tube containers are too bulky for field work and not well suited for mailing or transporting single test tubes. Also for single test tubes, a device useful for physical transportation or for mailing a contained test tube must not only protect the test tube from breakage but must also provide against leakage of the specimen to prevent possible contamination of other specimens. With presently used procedures, protection of the person transporting the specimens from exposure to potentially infectious substances is of increasing concern. Medical personnel and especially law enforcement personnel are often required to deliver specimens in test tubes housed only in paper or plastic envelopes. These envelopes do not prevent crushing the test tube, and leakage of the specimen often occurs once the test tube is broken and glass has puncture the envelope.

As will be shown in the following specification, the device according to the immediate invention overcomes the aforementioned disadvantages and provides other useful services for the storage and transportation of individual test tubes.

SUMMARY OF THE INVENTION

In practicing my invention, I have provided a tubular container sized to encase one typical laboratory test tube. My container is provided with a snap-on cap attached to an upper lip of the container by a living hinge. The snap-on cap is centrally affixed with a pliable washer which fits snugly against the container wall as a cap sealer. A tongue around the outside of the pliable washer fits into a groove around the inside of the container wall. The tongue and groove arrangement and the cap sealer makes the cap fit sufficiently tight to adequately seal against liquid from escaping the container. A protrusion on the front of the cap is provided as a thumb lever for removal of the cap. To maintain a glass test tube immobilized inside the container, I have reduced the bore in a bottom section of the container wall to closely proximate the size of the inserted test tube. The test tube fits snugly in a secure relationship with the lower section of my container. The bottom of my container is round to conform to the round bottom of the test tube. However, to prevent breakage of the encased test tube, the round bottom of the test tube is supported by a rounded test tube bottom support ledge and prevented from contacting the housing round bottom by a small opened cavity in the form of a separation chamber between the round end of the test tube and the round end of the container. The purpose of having the curved surface of the test tube round bottom resting against the curved surface of the round test tube bottom support ledge in that in case the lower area or bottom of my containment device became crushed the curved surface of rounded test tube bottom support ledge would tend to push the rounded surface of test tube round bottom upwards and save the encased test tube. I have also made provisions in my container for installing a foam or rubberized pad contoured to the shape of both my container and the bottom of the inserted test tube. The rubberized pad when placed in the separation chamber is further protection for the encased test tube.

To preserve specimens, glass test tubes are normally sealed with a rubbery stopper cap and for information purposes a label is usually affixed to the test tube wall. For viewing the encased test tube and being able to read labeling, my container is preferably manufactured of a clear transparent material such as plastic. So long as some recording means is available to ascertain the content of a test tube inside my container, however, my device is not necessarily restricted to a clear plastic, but the material of manufacture must be shatter resistant and be able to withstand jarring should rough transportation occur.

When a test tube is encased in my container restricted in the lower reduced bore part as described, most of the upper section of the test tube is free of my container wall and accessible from the top. This upper freedom of the test tube allows far easier retrieval of the encased test tube than would be possible if all wall areas of the test tube were closely confined within my container. The wider upper section of my container also tends to eliminate skidding of the rubber sealer top used in a majority of test tubes. These rubbery tops often stick or skid during test tube removal.

Therefore, a principal object of my invention is to provide a containment device for a single test tube in the form of a tubular container which maintains the test tube securely at the base and has wall areas clear of the test tube rubbery stopper to prevent stopper friction against the container wall during test tube retrieval.

Another object of the invention is to provide a containment device for test tubes in a container which has a removable liquid tight sealer cap with the cap attached to the container rim for immediate sealing when a specimen filled test tube is inserted.

A further object of the invention is to provide a container which is manufactured of a material difficult to shatter and in which a specimen filled test tube can be safely stored for future analysis or presentation of evidence in a court of law.

Other objects and the many advantages of the immediate invention will become known and understood with a reading of the specification and comparing numbered parts described with like numbered parts illustrated in the drawings.

DESCRIPTION OF THE PREFERRED EMBODIMENTS

Figures 1, 2:
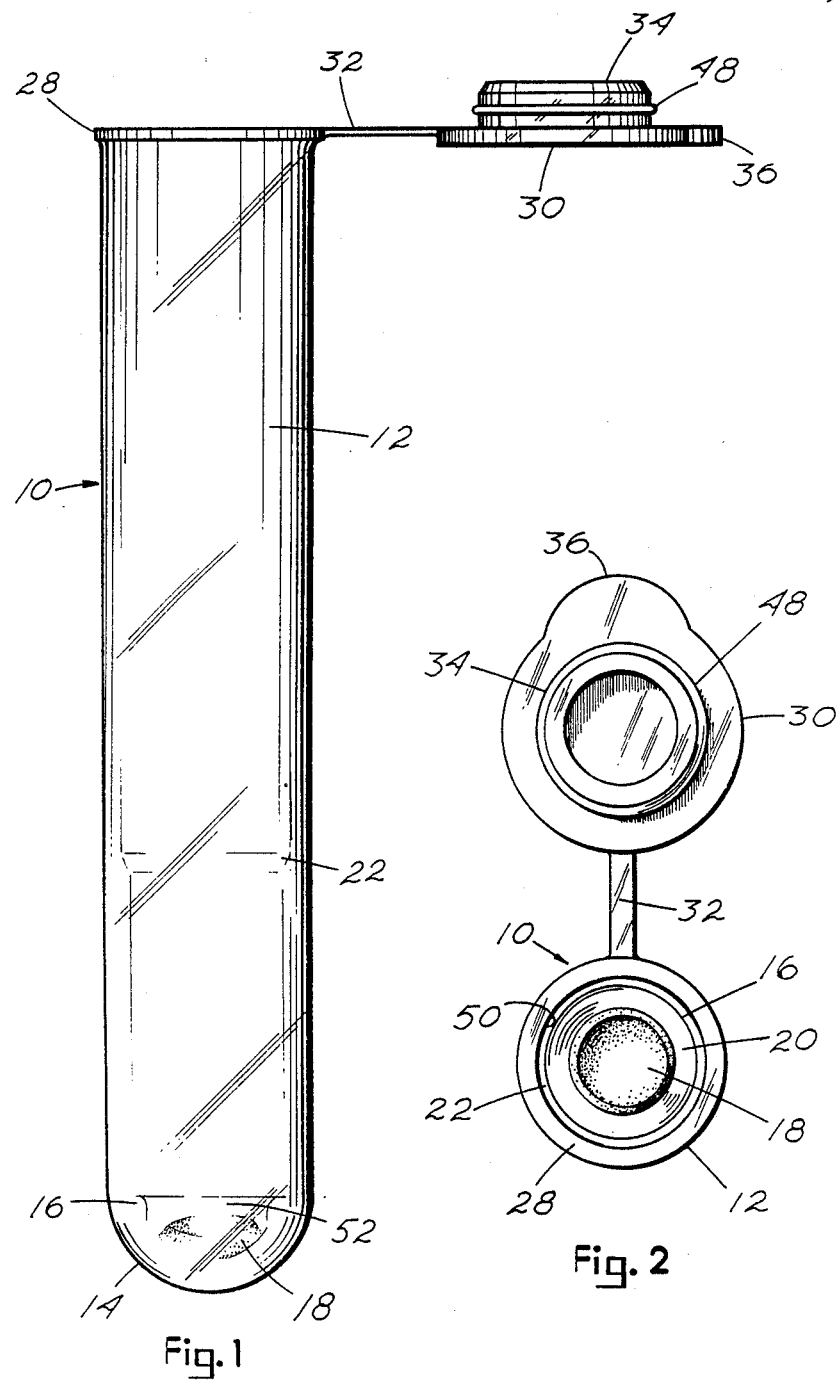
FIG. 1 shows the containment device for a test tube according to the invention from a side view in the form of a transparent container with a sealer cap.
FIG. 2 is a top plan view of the container with the sealer cap opened illustrating the living hinge cap attachment, the thumb release protrusion on the front of the cap, the cap sealer, and shows a top view of the inside of the container.

Referring now to the drawings at FIG. 1 where containment device 10 refers generally to the containment device for a test tubes according to the immediate invention. Containment device 10, as illustrated in FIG. 1, is formed elongated and tubular into tubular housing 12 rimmed at the opened top by housing cap seat rim 28 and closed at the bottom by housing round bottom 14. Although any shatter resistant material could be applicable for the structure of tubular housing 12, the preferred material as illustrated in the drawings is clear or semi-clear plastic such as polycarbonate for example. Attached to housing cap seat rim 28 by living cap hinge 32 is snap-in cap 30. For agent containment and sealing the open top of tubular housing 12, the center section of snap-in cap 30 is affixed with internal cap sealer 34 positioned to insert into the neck area of tubular housing 12 when snap-in cap 30 is closed. Internal cap sealer 34 is a pliable ring opened centrally to allow central expansion of the outer ring when internal cap sealer 34 is forced down into the opening of tubular housing 12 on the closing of snap-in cap 30. Snap-in cap 30, which is openable, waterproofs the top end of tubular housing 12 by pressure and a circular tongue and groove arrangement. The circular tongue is tongue 48 circumventing the external edge of internal cap sealer 34 and the groove is groove 50 inscribed adjacently below housing cap seat rim 28 in the upper wall of tubular housing 12. A protruding cap thumb release 36 is provided for assistance in removing snap-in cap 30 by upward thumb pressure under cap thumb release 36.

FIG. 2 shows snap-in cap 30 in a bottom plan view and tubular housing 12 in a top plan view. Round style snap-in cap 30 is affixed centrally by internal cap sealer 34 and at the outer edge is formed into a rounded levering extension cap thumb release 36 to help in opening the cap. Snap-in cap 30 attaches to tubular housing 12 at cap seat rim 28 retained by living cap hinge 32. Tongue 48 is on the outer edge of internal cap sealer 34. Looking down into the open end of containment device 10, groove 50 which accepts tongue 48 is at the top just under housing cap seat rim 28. Inside tubular housing 12, the reduced bore arrangement for supporting the base of test tube 40 is below bevel guide to reduced bore area 22 and designated reduced bore test tube support area 20. Rounded test tube bottom support ledge 16 can just be seen surrounding rubberized pad 18.

Figure 3:
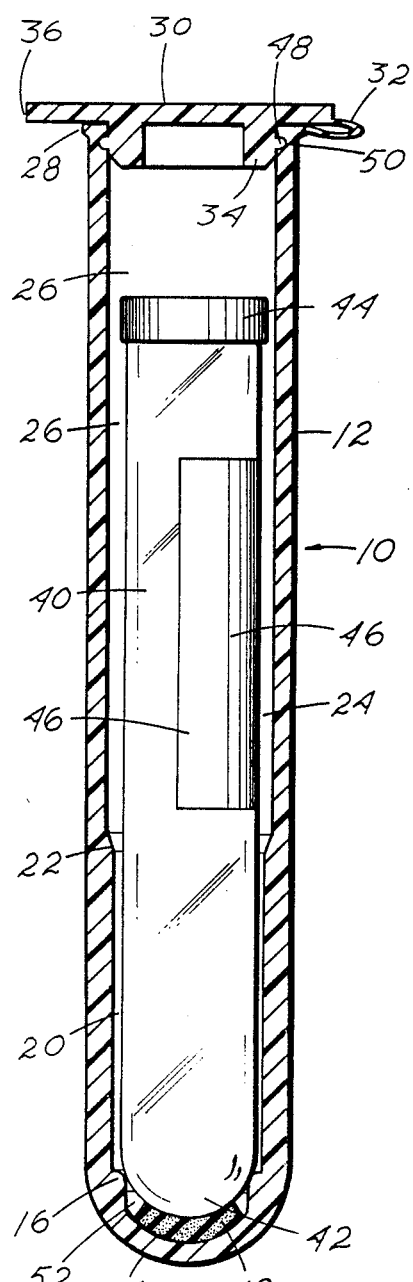
FIG. 3 is a sectional side view of the container illustrating the encased test tube retained by the smaller bore size of the lower section of the container and showing the rounded ridge top ledge of the separation chamber contacting and supporting the round bottom of the test tube support ring above a rubberized pad.

FIG. 3 shows containment device 10 in a sectional side view best illustrated the upper wide housing area 24 and the lower reduced bore test tube support area 20. Reduced bore test tube support area 20 is a downward narrowed section of tubular housing 12 sized to maintain test tube 40 restrictively positioned inside of tubular housing 12. This restrictively positioning of test tube 40 prevents the test tube upper wall, usually glass, from contacting the upper wall of tubular housing 12. Also test tube stopper top 44, usually rubbery, is prevented from restrictively rubbing along the wall of tubular housing 12 when test tube 40 is being retrieved. FIG. 3 also illustrates how test tube round bottom 42 is supported in rounded test tube bottom support ledge 16 and prevented from contacting housing rounded bottom 14 with or without rubberized pad 18 installed as shown in separation chamber 52. Rubberized pad 18 is an available added feature for further processing test tube round bottom 42 during encasement. However, separation chamber 52 provides a space between test tube round bottom 42 and housing round bottom 14 when test tube round bottom 42 rests on rounded test tube bottom support ledge 16. The purpose of having the curved surfaces of test tube round bottom 42 resting against the curved surface of rounded test tube buttom support ledge 16 is that in case the lower area or bottom of containment device 10 became crushed the curved surface of rounded test tube bottom support ledge 16 would tend to push the round surface of test tube round bottom 42 upward and save test tube 40 from being damaged.

At the top of tubular housing 12 in FIG. 3, snap-in cap 30 can be seen in the closed or sealed position. The under surface of snap-in cap 30 rests on the top surface of housing cap seat rim 28 and internal cap sealer 34 is pressured inside of tubular housing 12. Circumventing tongue 48 further seals the container opening by being snapped into groove 50 just below housing cap seat rim 28 in the wall of tubular housing 12. Clear plastic is considered the preferred material for fabrication of tubular housing 12 for the obvious reason that the positioning of test tube 40 can be seen and label 46, which indicates the content of test tube 40, can be read without removing test tube 40 from tubular housing 12. However, opaque material may be used for the manufacture of containment device 10. As illustrated in FIG. 3, an upper major portion of test tube 40 is free of the interior wall surface of tubular housing 12. This free upper portion is in retrieval space 26 which allows room to reach inside for withdrawal of test tube 40 from tubular housing 12 by instrument or even by fingers. Beveled guide to reduced bore area 22 is the downward angled upper wall ridge of reduced bore test tube support area 20. When test tube 40 is inserted into tubular housing 12, beveled guide 22 eases and directs test tube round bottom 42 into the smaller bore support area eliminating chances of cracking test tube 40 by sudden contact with a thickened wall ridge. Also, particular to the immediate invention is the principal purpose of the reduced bore test tube support area 20 as follows: As previously described, test tube 40 is normally sealed with a rubbery stopper, test tube stopper top 44. During retrieval of test tube 40 from inside of containment device 10, it is often necessary to upend and shake containment device 10 to force out test tube 40 angled or upside down. Reduced bore test tube support area 20 directs test tube 40 out of tubular housing 12 in a predictable alignment and manner without allowing test tube stopper top 44 to hang up or skid along the inside wall of tubular housing 12. In other straight wall containers, the rubbery top stopper 44 of a test tube frictionally contacting the inside container wall can become a serious problem during removal of the test tube from the container. In the immediate invention, that problem is eliminated.

Figure 4:
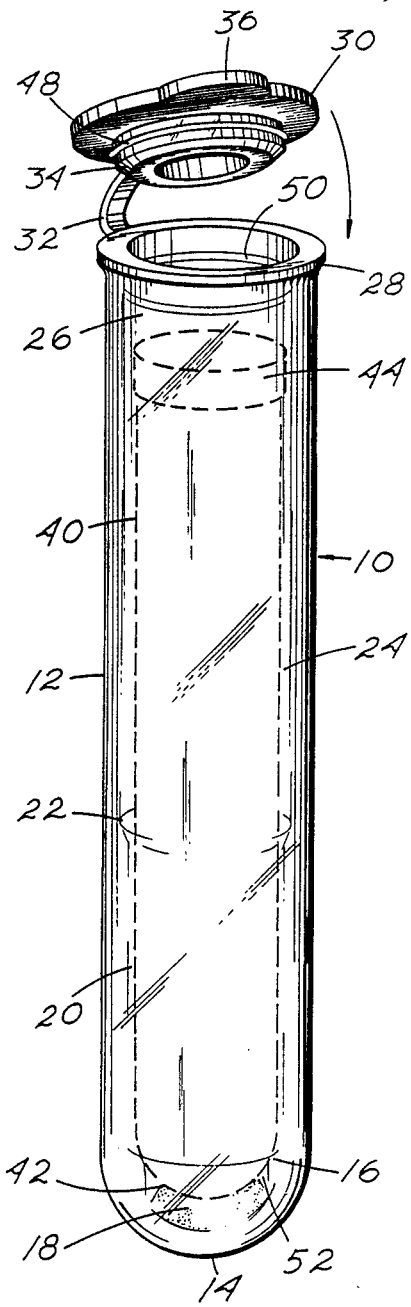
FIG. 4 is a perspective view of the container showing the encased test tube in dotted lines and the cap of the container positioned for sealing.

FIG. 4 shows containment device 10 in a perspective illustration. Test tube 40, illustrated by dotted lines, can be seen through the transparent walls of tubular housing 12 encased inside. Snap-in cap 30 is positioned to be closed doown on the opened top of tubular housing 12 placing snap internal cap sealer 34 inside of tubular housing 12 with tongue 48 in groove 50 sealing the top shut. With snap-in cap 30 sealed, test tube 40, with any biological samples inside, is adequately contained for packaging either for local transporting or for mailing. Test tube 40 protectively encased inside of containment device 10 can also be stored as a tube or packaged and stored with the tube content available as evidence in future law cases.

Even though I have described a preferred embodiment of my invention with considerable details and with drawn illustrations, it is to be understood that I may make changes to the invention which do not deviate from the intended scope of the appended claims and further that any changes made by others which fall within the intended scope of my claims, I will consider to be my invention.

What I claim as my invention is:

1. A protective containment device for a single test tube adapted to allow predictable retrieval of said test tube from said containment device, comprising;

a tubular housing adapted to receive and internally retain said test tube in longitudinal alignment with said tubular housing, said tubular housing having a closed first end and an oppositely disposed opened second end;

said tubular housing having a first and a second internal diameter, said first internal diameter being adjacent said closed first end extending a distance toward said open second end, said second internal diameter being adjacent said opened second end extending a distance toward said closed first end, said second internal diameter being larger than said first internal diameter, a tapering from said first internal diameter to said second internal diameter adapted to provide guidance to a rounded structurally closed end of said test tube when inserted into said tubular housing, said first internal diameter sized to receive said structurally closed end of said test tube providing lateral support to said test tube, said second internal diameter sized larger diametrically than a removable rubbery stopper on said test tube, said first internal diameter sized to maintain said test tube generally centered in said tubular housing with said centering adapted to maintain a separation between said rubbery stopper on said test tube and said second internal diameter, said separation maintained between said rubbery stopper and said second internal diameter adapted to provide smooth sliding of said stoppered test tube from said tubular housing providing said predictable retrieval;

a cap affixed to said opened second end of said tubular housing by a living hinge, said cap adapted to temporarily close said opened second end of said tubular housing;

means adapted to provide liquid tight sealing between said cap and said opened second end when said tubular housing is closed by said cap;

a rubbery pad within said tubular housing at said closed first end adapted to provide protective cushioned support to said rounded structurally closed end of said test tube when contained within said tubular housing;

said tubular housing being internally longitudinally longer than said stoppered test tube providing space between said rubbery stopper on said test tube and said cap when closed with said test tube fully inserted into said tubular housing toward said closed first end;

a rounded annular support ledge within said tubular housing between said closed first end and said first internal diameter, said support ledge encircling said rubbery pad, said support ledge adapted to contact said rounded structurally closed end of said test tube when said test tube is fully inserted into said tubular housing toward said closed first end, said support ledge adapted to cause said test tube to slide toward said opened second end of said tubular housing upon crushing of said closed first end;

said tubular housing and said cap manufactured of shatter resistant material.

2. The protective containment device as described in claim 1 wherein said means adapted to provide liquid tight sealing between said cap and said opened second end includes an annular tongue on said cap adapted to snap into a groove in said tubular housing.

3. The protective containment device as described in claim 1 wherein said shatter resistant material is a transparent plastic.

* * * * *